United States Patent [19]

Cozzi et al.

[11] Patent Number: 5,264,441

[45] Date of Patent: Nov. 23, 1993

[54] DISUBSTITUTED UREAS AND THIOUREAS DERIVATIVES

[75] Inventors: Paolo Cozzi; Danielle Fancelli; Dino Severino, all of Milan; Augusto Chiari, Florence; Giancarlo Ghiselli, Busto Arsizio, all of Italy

[73] Assignee: Farmitalia Carlo Erba S.r.l., Milan, Italy

[21] Appl. No.: 836,472

[22] Filed: Feb. 18, 1992

[30] Foreign Application Priority Data

Feb. 19, 1991 [GB] United Kingdom ............ 9103446
Apr. 3, 1991 [GB] United Kingdom ............ 9106961
Dec. 11, 1991 [GB] United Kingdom ............ 9126322

[51] Int. Cl.$^5$ .......... A61K 31/17; C07C 275/28; C07C 335/16
[52] U.S. Cl. .................. 514/336; 514/357; 514/397; 514/400; 514/431; 514/433; 514/436; 514/439; 514/440; 514/450; 514/463; 514/466; 514/467; 514/585; 514/586; 514/587; 514/596; 514/597; 514/598; 546/268; 546/283; 546/284; 548/311.7; 548/315.1; 548/315.4; 548/336.1; 564/27; 564/28; 564/29; 564/48; 564/52; 564/53; 564/54
[58] Field of Search ........ 549/11, 20, 35, 39, 549/60, 347, 373, 452, 441; 564/17, 16, 27, 28, 29, 47, 48, 53, 54; 511/431, 436, 446, 450, 452, 467, 464, 465, 466, 585, 586, 587, 596, 597, 598, 397, 336; 546/213, 281, 268

[56] References Cited

U.S. PATENT DOCUMENTS

| | | | |
|---|---|---|---|
| 4,387,105 | 6/1983 | DeVries et al. ............ | 564/52 |
| 4,623,662 | 11/1986 | DeVries et al. ............ | 514/598 |
| 5,003,106 | 3/1992 | DeVries ............ | 564/52 |
| 5,015,644 | 5/1991 | Roth et al. ............ | 564/52 |
| 5,063,247 | 11/1991 | Sekiya et al. ............ | 564/52 |

FOREIGN PATENT DOCUMENTS

| | | |
|---|---|---|
| 293880 | 12/1988 | European Pat. Off. . |
| 297610 | 1/1989 | European Pat. Off. . |
| 335374 | 10/1989 | European Pat. Off. . |
| 335375 | 10/1989 | European Pat. Off. . |
| 344425 | 12/1989 | European Pat. Off. . |
| 384320 | 8/1990 | European Pat. Off. . |
| 399422 | 11/1990 | European Pat. Off. . |
| 405233 | 1/1991 | European Pat. Off. . |
| 439059 | 7/1991 | European Pat. Off. . |
| 450660 | 10/1991 | European Pat. Off. . |
| 415123 | 3/1992 | European Pat. Off. . |

OTHER PUBLICATIONS

Derwent Abstract of JO-3223254; published Oct. 2, 1991.
Derwent Abstract of WO9015048; published Dec. 13, 1990.
Derwent Abstract of WO9113871; published Sep. 19, 1991.
Derwent Abstract of JO 3220168; published Sep. 27, 1991.
Derwent Abstract of WO9115464; published Oct. 17, 1991.
Abstract of Wo9117150; published Nov. 14, 1991.

*Primary Examiner*—Richard L. Raymond
*Attorney, Agent, or Firm*—Nikaido Marmelstein Murray & Oram

[57] ABSTRACT

The invention provides new ureas and thioureas derivatives of general formula (I)

$$A-(CH_2)_m-\underset{\underset{Y-R_2}{|}}{\overset{\overset{X-R_1}{|}}{C}}-(CH_2)_n-NH-\underset{\underset{Q}{\|}}{C}-NH-B \quad (I)$$

and pharmaceutically acceptable salts thereof, which are useful as therapeutic agents such as for the prevention of coronary heart disease and as antidyslipidaemic agents.

9 Claims, No Drawings

DISUBSTITUTED UREAS AND THIOUREAS DERIVATIVES

The present invention relates to new ureas and thioureas derivatives, to a process for their preparation and to pharmaceutical compositions containing them. The invention provides compounds having the following general formula (I)

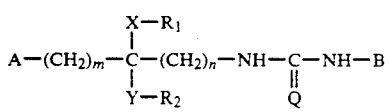

wherein
m is zero, 1 or 2;
n is 1, 2 or 3;
Q is oxygen or sulphur;
X and Y, being the same, are oxygen or sulphur;
A is
a) a $C_1$–$C_{10}$ saturated or unsaturated, branched or unbranched hydrocarbon chain, unsubstituted or substituted by 1 to 4 substituents independently chosen from halogen, $C_1$–$C_6$ alkyl, trihalo-$C_1$–$C_3$ alkyl and $C_1$–$C_6$ alkoxy;
b) a $C_3$–$C_7$ cycloalkyl ring unsubstituted or substituted by 1 to 4 substituents independently chosen from halogen, $C_1$–$C_6$ alkyl, trihalo-$C_1$–$C_3$ alkyl and $C_1$–$C_6$ alkoxy;
c) an aryl group unsubstituted or substituted by one to four substituents independently chosen from halogen, $C_1$–$C_6$ alkyl, trihalo-$C_1$–$C_3$ alkyl, hydroxy, $C_1$–$C_6$ alkoxy, $C_1$–$C_6$ alkylthio, $C_1$–$C_6$ alkylsulfonyl and $C_1$–$C_4$ di-alkylamino;
d) an aryl group substituted by two adjacent substituents forming a methylenedioxy group and optionally by 1 to 3 substituents as defined above under c); or
e) an aryl group substituted by an imidazolyl group, in its turn optionally substituted by $C_1$–$C_4$ alkyl;
each of $R_1$ and $R_2$, independently, is $C_1$–$C_6$ alkyl; or $R_1$ and $R_2$, taken together, are a $C_2$–$C_4$ alkylene chain in which each carbon atom can be optionally substituted by 1 or 2 substituents independently chosen from halogen and $C_1$–$C_4$ alkyl;
B is an aryl group unsubstituted or substituted by 1 to 4 substituents independently chosen from halogen, $C_1$–$C_6$ alkyl, trihalo-$C_1$–$C_3$ alkyl, $C_1$–$C_6$ alkoxy, $C_1$–$C_6$ alkylthio, and $C_1$–$C_6$ alkylsulfonyl; and the pharmaceutically acceptable salts thereof.

The invention includes within its scope all the possible isomers, stereoisomers, and their mixtures and the metabolites and the metabolic precursors or bio-precursors of the compounds of formula (I).

The alkyl, alkoxy, alkylthio, di-alkylamino and alkylsulfonyl groups may be branched or straight chain groups. A $C_3$–$C_7$ cycloalkyl group is preferably cyclopentyl or cyclohexyl. A $C_1$–$C_6$ alkyl group is e.g. a $C_1$–$C_4$ alkyl group, in particular methyl, ethyl, propyl or butyl. A $C_1$–$C_4$ alkyl group is preferably methyl or ethyl. A $C_1$–$C_6$ alkoxy group is preferably methoxy, ethoxy, propoxy or isopropoxy, in particular methoxy or ethoxy. A $C_1$–$C_6$ alkylthio group is e.g. methylthio, ethylthio, propylthio, or butylthio, in particular methylthio and ethylthio. A $C_1$–$C_6$ alkylsulfonyl group is e.g. methylsulfonyl, ethylsulfonyl, propylsulfonyl, in particular methylsulfonyl. A halogen atom is e.g. chlorine, bromine, or fluorine, in particular chlorine or fluorine. A trihalo-$C_1$–$C_3$ alkyl group is e.g. a trichloro- or trifluoro $C_1$–$C_3$ alkyl group, in particular trifluoromethyl. A $C_1$–$C_4$ di-alkylamino group is preferably a dimethyl- or diethylamino group, in particular a dimethylamino group. Each of A and B as an aryl group may be both an aromatic e.g. phenyl or naphthyl, in particular a phenyl ring, and a heteromonocyclic ring. Said heteromonocyclic ring may contain from 1 to 3 heteroatoms independently chosen from nitrogen, sulfur, and oxygen; and preferably it is a thienyl or pyridyl ring, in particular 2- or 3-thienyl. When A is an aryl group substituted by an unsubstituted imidazolyl group, then the imidazolyl group may be an imidazol-1-yl, imidazol-2-yl or imidazol-4(5)-yl group, in particular an imidazol-1-yl or imidazol-2-yl group. Alternatively, when A is an aryl group substituted by a $C_1$–$C_4$ alkyl substituted imidazolyl group, then said imidazolyl group may be in particular a 1-($C_1$–$C_4$ alkyl)-imidazol-2-yl or a 2-($C_1$–$C_4$ alkyl)-imidazol-1-yl group.

When A is a $C_1$–$C_{10}$ hydrocarbon chain, said chain is preferably a $C_4$–$C_{10}$, in particular $C_4$–$C_7$ hydrocarbon chain optionally containing 1 or 2 double or triple bonds. A $C_3$–$C_7$ cycloalkyl ring is preferably cyclopentyl or cyclohexyl; when said ring is substituted by halogen, the halogen is preferably fluorine.

It is evident that when $R_1$ and $R_2$, taken together are a $C_2$–$C_4$ alkylene chain and X and Y are oxygen, then the pentatomic, hexatomic or heptatomic resulting 1,3-dioxalkyl ring is respectively a 1,3-dioxolan, 1,3-dioxan or 1,3-dioxepan ring which may be represented by the following chemical formula

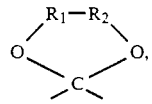

wherein $R_1$–$R_2$ represents a $C_2$–$C_4$ alkylene chain in which each carbon atom may be optionally substituted by 1 or 2 substituents independently chosen from halogen, in particular fluorine, and $C_1$–$C_4$ alkyl.

Analogously, when $R_1$ and $R_2$, taken together, are a $C_2$–$C_4$ alkylene chain and X and Y are sulfur, then the pentatomic, hexatomic, or heptatomic resulting 1,3-dithiaalkyl ring is respectively a 1,3-dithiolan, 1,3-dithian, or 1,3-dithiepan ring which may be represented by the following chemical formula

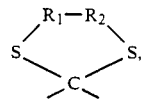

wherein $R_1$–$R_2$ represents a $C_2$–$C_4$ alkylene chain in which each carbon atom may be optionally substituted by 1 or 2 substituents independently chosen from halogen, in particular fluorine, and $C_1$–$C_4$ alkyl.

Pharmaceutically acceptable salts of the compounds of the invention include acid addition salts, with inorganic, e.g. nitric, hydrochloric, hydrobromic, sulphuric, perchloric and phosphoric acids, or organic, e.g. acetic, propionic, glycolic, lactic, oxalic, malonic, malic, maleic, tartaric, citric, benzoic, cinnamic, mandelic and salicylic acids.

As stated above, the present invention also includes within its scope pharmaceutically acceptable bioprecursors (otherwise known as pro-drugs) of the compounds of formula (I), i.e. compounds which have a different formula to formula (I) above but which nevertheless upon administration to a human being are converted directly or indirectly in vivo into a compound of formula (I).

Preferred compounds of the invention are the compounds of formula (I), wherein
m is zero or 1;
n is 1, 2 or 3;
Q is oxygen or sulphur;
X and Y, being the same, are oxygen or sulphur;
$R_1$ and $R_2$, taken together, form a $C_2$-$C_4$ alkylene chain in which each carbon atom can be unsubstituted or substituted by one or two substituents independently chosen from halogen and $C_1$-$C_4$ alkyl;
A is
  a') a branched or unbranched $C_4$-$C_7$ hydrocarbon chain optionally containing 1 or 2 double bonds, unsubstituted or substituted by one or two substituents chosen independently from halogen and trifluoromethyl;
  b') a cyclopentyl or cyclohexyl ring unsubstituted or substituted by one or two substituents chosen independently from halogen and $C_1$-$C_4$ alkyl;
  c') a phenyl or pyridyl ring unsubstituted or substituted by one or two substituents independently chosen from halogen, $C_1$-$C_4$ alkyl, trifluoromethyl, hydroxy, $C_1$-$C_4$ alkoxy, $C_1$-$C_4$ alkylsulfonyl and $C_1$-$C_4$ di-alkylamino;
  d') a phenyl ring substituted by two adjacent substituents forming a methylenedioxy group and optionally by one or two substituents as defined above under c'); or
  e') a phenyl ring substituted by an imidazolyl group, in its turn optionally substituted by $C_1$-$C_4$ alkyl;
B is a phenyl ring unsubstituted or substituted by one or two substituents independently chosen from halogen, $C_1$-$C_4$ alkyl and $C_1$-$C_4$ alkoxy; and the pharmaceutically acceptable salts thereof.

More preferred compounds of the invention are the compounds of formula (I), wherein
m is zero or 1;
n is 1 or 2;
Q is oxygen;
X and Y, being the same, are oxygen;
$R_1$ and $R_2$, taken together, form a $C_2$-$C_3$ alkylene chain in which at least one carbon atom is substituted by one or two substituents independently chosen from halogen and $C_1$-$C_4$ alkyl;
A is a $C_4$-$C_7$ alkyl chain; a cyclopentyl or cyclohexyl ring unsubstituted or substituted by one or two substituents independently chosen from halogen and $C_1$-$C_4$ alkyl; or a phenyl or pyridyl ring unsubstituted or substituted by one or two substituents independently chosen from halogen, $C_1$-$C_4$ alkyl, hydroxy and $C_1$-$C_4$ alkyl di-alkylamino;
B is a phenyl ring substituted by one or two substituents independently chosen from halogen and $C_1$-$C_4$ alkyl; and the pharmaceutically acceptable salts thereof.

A class of more preferred compounds of the invention are also the compounds of formula (I), wherein
m is zero or 1;
n is 1 or 2;
Q is oxygen;
X and Y, being the same, are sulphur;
$R_1$ and $R_2$, taken together, form a $C_2$-$C_3$ alkylene chain in which each carbon atom can be unsubstituted or substituted independently by one or two substituents independently chosen from halogen and $C_1$-$C_4$ alkyl;
A is a $C_4$-$C_7$ alkyl chain; a cyclopentyl or cyclohexyl ring unsubstituted or substituted by one or two substituents independently chosen from halogen and $C_1$-$C_4$ alkyl;
B is a phenyl ring substituted by one or two substituents independently chosen from halogen and $C_1$-$C_4$ alkyl; and the pharmaceutically acceptable salts thereof.

Examples of preferred compounds of the invention are the following:

N-[2,6-bis(1-methylethyl)phenyl]-N'-(2-phenyldioxolan-2-yl)methylurea;

N-[2,6-bis(1-methylethyl)phenyl]-N'-(5,5-dimethyl-2-phenyl-1,3-dioxan-2-yl)methylurea;

N-[2,6-bis(1-methylethyl)phenyl]-N'-]5,5-dimethyl-2-(4-fluorophenyl)-1,3-dioxan-2-yl]methylurea;

N-[2,6-bis(1-methylethyl)phenyl]-N'-[4,5-dimethyl-2-phenyldioxolan-2-yl]methylurea;

N-[2,6-bis(1-methylethyl)phenyl]-N'-[5,5-diethyl-2-phenyl-1,3-dioxan-2-yl]methylurea;

N-[2,6-bis(1-methylethyl)phenyl]-N'-[2-cyclohexyl-5,5-dimethyl-1,3-dioxan-2-yl]methylurea;

N-[2,6-bis(1-methylethyl)phenyl]-N'-[2-cyclohexyl-4,5-dimethyl-dioxolan-2-yl]methylurea;

N-[2,6-bis(1-methylethyl)phenyl]-N'-[2-cyclopentyl-5,5-dimethyl-1,3-dioxan-2-yl]methylurea;

N-[2,6-bis(1-methylethyl)phenyl]-N'-(2-cyclohexyl-5,5-diethyl-1,3-dioxan-2-yl)methylurea;

N-[2,6-bis(1-methylethyl)phenyl]-N'-(2-cyclohexyl-1,3-dithiolan-2-yl)methylurea;

N-[2,6-bis(1-methylethyl)phenyl]-N'-[2-(4-dimethylaminophenyl)-5,5-dimethyl-1,3-dioxan-2-yl]methylurea;

N-[2,6-bis(1-methylethyl)phenyl]-N'-[2-cyclohexyl-1,3-dithian-2-yl]methylurea;

N-[2,6-bis(1-methylethyl)phenyl]-N'-[2-phenyl-1,3-dithiolan-2-yl]methylurea;

N-[2,6-bis(1-methylethyl)phenyl]-N'-(2-phenyl-1,3-dithian-2-yl)methylurea;

N-[2,6-bis(1-methylethyl)phenyl]-N'-(2-heptyl-1,3-dithiolan-2-yl)methylurea;

N-[2,6-bis(1-methylethyl)phenyl]-N'-(2-heptyl-5,5-dimethyl-1,3-dioxan-2-yl)methylurea;

N-[2,6-bis(1-methylethyl)phenyl]-N'-[4,5-dimethyl-2-(4-dimethylaminophenyl)-1,3-dioxolan-2-yl]methylurea;

N-[2,6-bis(1-methylethyl)phenyl]-N'-[2-(4-dimethylaminophenyl)-1,3-dithian-2-yl]methylurea;

N-[2,6-bis(1-methylethyl)phenyl]-N'-(4,5-dimethyl-2-cyclohexyldithiolan-2-yl)methylurea; and N-[2,6-bis(1-methylethyl)phenyl]-N'-[2-(4-dimethylaminophenyl)dithiolan-2-yl]methylurea;

if the case either as a single isomer or as a mixture of isomers thereof, and the pharmaceutically acceptable salts thereof.

The compounds of the invention can be obtained by a process comprising:
a) reacting a compound of formula (II)

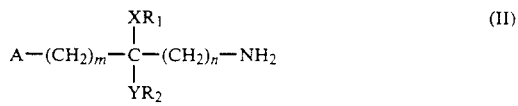

wherein A, m, n, X, Y, $R_1$ and $R_2$ are as defined above, with an isocyanate or isothiocyanate of formula (III)

$$B-N=C=Q \qquad (III)$$

wherein B and Q are as defined above; or b) reacting a compound of formula (IV)

$$A-(CH_2)_m-\underset{\underset{YR_2}{|}}{\overset{\overset{XR_1}{|}}{C}}-(CH_2)_n-N=C=Q \qquad (IV)$$

wherein A, Q, m, n, X, Y, $R_1$ and $R_2$ are as defined above with an amine of formula (V)

$$B-NH_2 \qquad (V)$$

wherein B is as defined above; and, if desired, converting a compound of formula (I) into another compound of formula (I), and/or resolving a mixture of isomers of compounds of formula (I) into the single isomers, and/or converting a compound of formula (I) into a pharmaceutically acceptable salt thereof.

The reaction of a compound of formula (II) with a compound of formula (III) and the reaction of a compound of formula (IV) with a compound of formula (V), respectively, is an analogy process and can be carried out according to well known methods in the art. For instance these reactions can be performed in a suitable organic solvent e.g. ethyl acetate or n-hexane or opportune mixture of the two, at a temperature ranging from room temperature to reflux temperature of the reacting mixture.

The compounds of formula (II) can be prepared from the corresponding aryl-, alkyl-, or cycloalkylhalomethylketones, that are either commercially available or may be easily synthesized from commercially available starting materials by methods well known in the art, via halogen, e.g. bromine, replacement with alkali metal phthalimide, preferably potassium phthalimide, ketalization or thioketalization, and final hydrolysis of the phthalimido group, according to known methods in the art.

The isocyanates and isothiocyanates of formula (III) are known compounds or may be obtained by known methods from the corresponding amino-compounds.

Compounds of formula (IV) may be obtained by reacting compounds of formula (II) with phosgene or thiophosgene according to known processes.

The amines of formula (V) are known or commercially available, or, if not previously known, may be easily synthesized from commercially available starting materials by methods well known in the art.

The optional conversion of a compound of formula (I) into another compound of formula (I), as well as the separation of a mixture of isomers of a compound of the invention into the single isomers, or the conversion of a compound of formula (I) into a pharmaceutically acceptable salt thereof, can be carried out according to well known methods in the art.

PHARMACOLOGY

The compounds of the invention show inhibitory activity of the enzyme acyl CoA:cholesterol acyltransferase (ACAT-EC 2.3.1.26) which regulates the intracellular esterification of cholesterol (Suckling K. E., Stange E. F., J. Lip. Res. (1985) 26, 647) and thus the intracellular accumulation of cholesteryl esters. The activity of this enzyme increases to the greatest extent during the atherosclerotic process in which the accumulation of esterified cholesterol in the atherosclerotic plaque is one of the predominant events (Brecher P., Chan C., B.B.A. (1980) 617, 458). ACAT also plays a key role in the intestinal absorption of cholesterol and a significant activity of the enzyme has been observed in intestinal mucosa cells from several animal species (Heider J. G., Pickens C. E., Kelly L. A. [J. Lip. Res. (1983) 24, 1127]. By virtue of their ACAT inhibitory activity the compounds of this invention, besides having antidyslipidaemic activity, act also as direct antiatherosclerotic agents, able to inhibit the development of the atheromatous plaque, and therefore are useful in particular for the prevention of coronary heart disease (CHD), e.g. myocardial infarction and angina. The activity of the enzyme and its regulation by the compounds of the invention has been evaluated in our laboratories on microsomal preparations from atherosclerotic rabbit thoracic aorta, essentially according to F. P. Bell (Atherosclerosis (1981), 38, 81). Table 1 exemplifies the results obtained by testing for instance a representative group of compounds according to this invention:

N-[2,6-bis(1-methylethyl)phenyl]-N'-(2-cyclohexyl-1,3-dithiolan-2-yl)methylurea (internal code FCE 27612);

N-[2,6-bis(1-methylethyl)phenyl]-N'-(2-cyclohexyl-5,5-dimethyl-1,3-dioxan-2-yl)methylurea (internal code FCE 27356);

N-[2,6-bis(1-methylethyl)phenyl]-N'-(2,2-diethoxy-2-phenyl) ethylurea (internal code FCE 27020) and the known compound CL 277082 whose inhibitory activity in vitro has been already demonstrated (J. Med. Chem. (1986), 29, 1131–1133).

TABLE I

| $IC_{50}$ values for the inhibition activity in microsomes from atherosclerotic rabbit thoracic aortae. | |
|---|---|
| COMPOUND | $IC_{50}$ (M) |
| FCE 27612 | $9.50 \cdot 10^{-9}$ |
| FCE 27356 | $6.50 \cdot 10^{-9}$ |
| FCE 27020 | $7.47 \cdot 10^{-9}$ |
| CL 277082 | $1.50 \cdot 10^{-7}$ |

The values of $IC_{50}$ for the ACAT inhibition in rabbit aorta provide evidence that the compounds of the invention are more potent than CL 277082. Moreover, the compounds of the invention are useful as antidyslipidaemic agents, indeed they show a high activity in lowering total serum cholesterol and triglycerides. For example the compound of the invention coded FCE 27050 added to the diet had remarkable hypolipidaemic effect in Sprague-Dawley rats fed a 1.5% cholesterol-enriched chow for a week. In this experimental model $ED_{50}$ values calculated for the cholesterol lowering effect in plasma and liver were 0.83 and 0.51 mg/kg/day respectively. The same compound added to the diet had potent hypolipidaemic effect and prevented the accumulation of cholesterol in the liver of New Zealand White rabbits fed a 1% cholesterol-enriched diet for 30 days. $ED_{50}$ values calculated for the cholesterol lowering effect in plasma and liver were 0.19 and 0.16 mg/kg/day respectively. Finally, the same compound given acutely at an oral dose of 10 mg/kg to albino mice fed a 1.5% cholesterol-enriched diet for seven hours, prevented in a significative fashion the accumulation of cholesterol in the liver of the animals. Table II exemplifies the results obtained by testing the hypolipidaemic activity of a representative group of compounds of the invention administered at the dose of 1 mg/kg/day to Sprague-Dawley rats fed 1.5% cholesterol-enriched diet for a week.

TABLE II

Hypocholesterolaemic activity of FCE compounds given at 1 mg/kg/day to rats fed 1.5% cholesterol-enriched diet for a week.

| Compound | Blood Total Cholesterol (mg/dl) | | % Change |
|---|---|---|---|
| | Control Mean ± SE (n = 9) | Treating Mean ± SE (n = 9) | |
| FCE 27050 | 156 ± 14 | 62 ± 5* | −60 |
| FCE 27529 | 195 ± 16 | 75 ± 4* | −62 |
| FCE 27612 | 212 ± 24 | 59 ± 7* | −72 |
| FCE 27480 | 156 ± 14 | 85 ± 9* | −46 |
| FCE 27607 | 212 ± 24 | 110 ± 8* | −48 |

*p ≦ 0.01 (Dunnett's test)

In Table II internal code FCE 27050 means N-[2,6-bis(1-methylethyl)phenyl]-N'-[(2RS,4RS,5RS)-4,5-dimethyl-2-phenyldioxolan-2-yl]methylurea; internal code FCE 27529 means N-[2,6-bis(1-methylethyl)-phenyl]-N'-[(4R,5R)-4,5-dimethyl-2-phenyldioxolan-2-yl]methylurea; internal code FCE 27612 means N-[2,6-bis(1-methylethyl)phenyl]-N'-(2-cyclohexyl-1,3-dithiolan-2-yl)methylurea; internal code FCE 27480 means N-[2,6-bis(1-methylethyl)phenyl]-N'-[(4S, 5S)-2-cyclohexyl-4,5-dimethyldioxolan-2-yl]methylurea; and internal code FCE 27607 means N-[2,6-bis(1-methylethyl) phenyl]-N'-[2-(4-dimethylaminophenyl)-5,5-dimethyl-1,3-dioxan-2-yl]methylurea.

The dosage level suitable for oral administration to adult humans of the compounds of the invention may range from about 50 mg to about 500 mg per dose 1 to 3 times a day, depending on the disease, age and weight of the patients involved. For example, N-[2,6-bis(1-methylethyl)phenyl]-N'-(2-cyclohexyl-1,3-dithiolan-2-yl) methylurea is suitably administered orally at a dose in this range. The toxicity of the compounds of the invention is negligible, therefore they can be safely used in therapy. Nine hours food deprived mice and rats were treated orally with single administration of increasing doses, then housed and normally fed. The orientative acute toxicity ($LD_{50}$) was assessed on the seventh day after the treatment, for instance in the mouse after oral administration. The compounds of the invention can be administered in a variety of dosage forms, e.g. orally, in the form of tablets, capsules, sugar- or film-coated tablets, liquid solutions or suspension. The invention includes pharmaceutical compositions comprising a compound of the invention in association with a pharmaceutically acceptable excipient (which can be a carrier or diluent).

The pharmaceutical compositions comprising the compounds of the invention are typically prepared following conventional methods and are administered in a pharmaceutically suitable form.

For example, the solid oral forms may comprise, together with the active compound, diluents, e.g. lactose, dextrose, saccharose, cellulose, corn starch or potato starch; lubricants, e.g. silica, talc, stearic acid, magnesium or calcium stearate, and/or polyethylene glycols; binding agents, e.g. starches, arabic gums, gelatin, methylcellulose, carboxymethylcellulose or polyvinyl pyrrolidone; disaggregating agents, e.g. starch, alginic acid, alginates or sodium starch glycolate; effervescing mixtures; dyestuffs; sweeteners; wetting agents, such as lecithin, polysorbates, laurylsulphates; and, in general, non-toxic and pharmacologically inactive substances used in pharmaceutical formulations.

Said pharmaceutical preparations may be manufactured in known manner, for example, by means of mixing, granulating, tabletting, sugar-coating, or film-coating processes. The liquid dispersions for oral administration may be e.g. syrups, emulsions, and suspensions. The syrups may contain as carrier, for example, saccharose or saccharose with glycerine and/or mannitol and/or sorbitol; in particular a syrup to be administered to diabetic patients can contain as carriers only products not metabolizable to glucose, or metabolizable in very small amount to glucose, for example sorbitol.

The suspensions and the emulsions may contain as carrier, for example, a natural gum, agar, sodium alginate, pectin, methylcellulose, carboxymethylcellulose, or polyvinyl alcohol.

The following examples illustrate but do not limit the invention:

EXAMPLE 1

To a solution of (2-phenyl-dioxolan-1-yl)methylamine (1.79 g 0.10 mole) in 60 ml of n-hexane/ethylacetate (4:1) is added dropwise at room temperature 2,6-bis(1-methylethyl)phenylisocyanate (1.94 g, 0.105 mole). The reaction mixture is stirred at room temperature for five hours. Precipitated solid is filtered, washed with n-pentane/ether (1:1) and dried, yielding 3.10 g of N-[2,6-bis(1-methylethyl)phenyl]-N'-(2-phenyldioxolan-2-yl)methylurea;

white powder m.p. 144°–146° C.

Elemental analysis

| | C | H | N |
|---|---|---|---|
| calculated for $C_{23}M_{30}N_2O_3$ | 72.22 | 7.90 | 7.32 |
| found | 72.22 | 7.85 | 7.26 |

EXAMPLE 2

To a solution of (5,5-dimethyl-2-phenyl-1,3-dioxan-2-yl) methylurea (2.21 g, 0.10 mole) in 40 ml of ethylacetate is added dropwise at room temperature 2,6-bis(1-methylethyl) phenylisocyanate (1.94 g 0.105 mole). The reaction mixture is stirred at room temperature for sixteen hours. Volatiles are removed under reduced pressure and the residue is crystallized from ethylacetate/n-hexane yielding 3.45 g of N-[2,6-bis(1-methylethyl)phenyl]-N'-(5,5-dimethyl-2-phenyl-1,3-dioxan-2-yl)methylurea; white powder m.p. 168°–170° C.

Elemental analysis

| | C | H | N |
|---|---|---|---|
| calculated for $C_{26}M_{36}N_2O_3$ | 73.55 | 8.55 | 6.60 |
| found | 73.50 | 8.50 | 6.56 |

Analogously the following compounds can be prepared:

N-[2,6-bis(1-methylethyl)phenyl]-N'-(2,2-diethoxy-2-phenyl)ethylurea,
m.p. 134°–136° C.;

N-[2,6-bis(1-methylethyl)phenyl]-N'-[(2RS, 4RS, 5RS)-4,5-dimethyl-2-phenyldioxolan-2-yl]methylurea, m.p. 176°-178° C.; N-[2,6-bis(1-methylethyl)phenyl]-N'-[5,5-dimethyl-2-(4-fluorophenyl)-1,3-dioxan-2-yl]methylurea,
m.p. 173°-174° C.;
N-phenyl-N'-(2,2-dimethoxy-2-phenyl)ethylurea;
N-(2,4-dimethoxyphenyl)-N'-(2-phenyldioxolan-2-yl)methylurea;
N-(2,6-dibromophenyl)-N'-(2-phenyldioxolan-2-yl)methylurea;
N-(2,6-diethylphenyl)-N'-(2-phenyldioxolan-2-yl)methylurea;
N-(2,4-difluorophenyl)-N'-(2-phenyldioxolan-2-yl)methylurea;
N-[2,6-bis(1-methylethyl)phenyl]-N'-[2-(4-fluorphenyl)-dioxolan-2-yl]methylurea;
N-[2,6-bis(1-methylethyl)phenyl]-N'-[2-(4-chlorophenyl)dioxolan-2-yl]methylurea;
N-[2,6-bis(1-methylethyl)phenyl]-N'-[2-(2-chlorophenyl)dioxolan-2-yl]methylurea;
N-[2,6-bis(1-methylethyl)phenyl]-N'-[2-(2,6-difluorophenyl)dioxolan-2-yl]methylurea;
N-[2,6-bis(1-methylethyl)phenyl]-N'-(2-phenyl-1,3-dioxan-2-yl)methylurea;
N-[2,6-bis(1-methylethyl)phenyl]-N'-(2-benzyldioxolan-2-yl)methylurea;
N-[2,6-bis(1-methylethyl)phenyl]-N'-[(4R,5R)-4,5-dimethyl-2-phenyldioxolan-2-yl]methylurea,
m.p. 199°-201° C. $[\alpha]_D^{26} = -18.6$ (c=0.787, AcOH);
N-[2,6-bis(1-methylethyl)phenyl]-N'-[(4S,5S)-4,5-dimethyl-2-phenyldioxolan-2-yl]methylurea,
m.p. 199°-201° C. $[\alpha]_D^{26} = +18.6$ (c=0.650, AcOH);
N-[2,6-bis(1-methylethyl)phenyl]-N'-[(2S,4R,5S)-4,5-dimethyl-2-phenyldioxolan-2-yl]methylurea,
m.p. 159°-160° C.;
N-[2,6-bis(1-methylethyl)phenyl]-N'-[5,5-diethyl-2-phenyl-1,3-dioxan-2-yl]methylurea,
m.p. 139°-141° C.;
N-[2,6-bis(1-methylethyl)phenyl]-N'-[5,5-dimethyl-2-(4-bromophenyl)-1,3-dioxan-2-yl]methylurea,
m.p. 201°-203° C.;
N-[2,6-bis(1-methylethyl)phenyl]-N'-[5,5-dimethyl-2-(3-bromophenyl)-1,3-dioxan-2-yl]methylurea,
m.p. 154°-156° C.;
N-[2,6-bis(1-methylethyl)phenyl]-N'-[5,5-dimethyl-2-(3,4-methylenedioxylphenyl)-1,3-dioxan-2-yl]methylurea,
m.p. 178°-180° C.;
N-(2,4-difluorophenyl)-N'-(5,5-diethyl-2-phenyl-1,3-dioxan-2-yl)methylurea,
m.p. 147°-149° C.;
N-[2,6-bis(1-methylethyl)phenyl]-N'-[5-methyl-2-phenyl-5-propyl-1,3-dioxan-2-yl]methylurea;
N-[2,6-bis(1-methylethyl)phenyl]-N'-[5,5-dimethyl-2-(pyrid-4-yl)-1,3-dioxan-2-yl]methylurea; and
N-[2,6-bis(1-methylethyl)phenyl]-N'-[5,5-dimethyl-2-(thien-3-yl)-1,3-dioxan-2-yl]methylurea.

EXAMPLE 3

To a stirred solution of (2-cyclohexyl-5,5-dimethyl-1,3-dioxan-2-yl)methylamine (2.27 g 0.100 mole) in 40 ml of n-hexane/ethylacetate (5:1) is added dropwise at room temperature 2,6-bis(1-methylethyl)phenylisocyanate (1.94 g 0.105 mole). The reaction mixture is stirred at room temperature for two hours. Precipitated solid is filtered, washed with n-pentane/ether (1:1) and dried, yielding 3.85 g of N-[2,6-bis(1-methylethyl)phenyl]-N'-(2-cyclohexyl-5,5-dimethyl-1,3-dioxan-2-yl)methylurea.
White powder m.p. 188°-190° C.

| Elemental analysis | C | H | N |
|---|---|---|---|
| calculated for $C_{26}H_{42}N_2O_3$ | 72.51 | 9.83 | 6.50 |
| found | 72.50 | 9.89 | 6.45 |

EXAMPLE 4

To a stirred solution of [(4R, 5R)-2-cyclohexyl-4,5-dimethyldioxolan-2-yl]methylamine (2.13 g 0.100 mole) in 40 ml of ethylacetate is added dropwise at room temperature 2,6-bis(1-methylethyl)phenylisocyanate (1.94 g 0.105 mole). The reaction mixture is stirred at room temperature for two hours. Volatiles are removed under reduced pressure and the residue is crystallized from ethylacetate/n-hexane, yielding 3.45 g of N-[2,6-bis(1-methylethyl)phenyl]-N'-[(4R,5R)-2-cyclohexyl-4,5-dimethyl-dioxolan-2-yl]methylurea, $[\alpha]_D^{26} = -9.1$ (C=0.653, AcOH).
White powder m.p. 160°-162° C.

| Elemental analysis | C | H | N |
|---|---|---|---|
| calculated for $C_{25}H_{40}N_2O_3$ | 72.07 | 9.67 | 6.72 |
| found | 72.11 | 9.70 | 6.71 |

Analogously the following compounds can be prepared:
N-(2,4-difluorophenyl)-N'-(2-cyclohexyl-5,5-dimethyl-1,3-dioxan-2-yl)methylurea;
m.p. 205°-207° C.
N-[2,6-bis(1-methylethyl)phenyl]-N'-(2-cyclopentyl-5,5-dimethyl-1,3-dioxan-2-yl)methylurea;
m.p. 199°-201° C.
N-[2,6-bis(1-methylethyl)phenyl]-N'-(2-cyclopentyl-5,5-diethyl-1,3-dioxan-2-yl)methylurea;
m.p. 200°-202° C.
N-[2,6-bis(1-methylethyl)phenyl]-N'-(2-cyclohexyl-5,5-diethyl-1,3-dioxan-2-yl)methylurea;
m.p. 183°-185° C.
N-[2,6-bis(1-methylethyl)phenyl]-N'-(2,2-diethoxy-2-cyclohexyl)ethylurea;
N-(2,6-dimethylphenyl)-N'-(2-cyclohexyldioxolan-2-yl)methylurea;
N-[2,6-bis(1-methylethyl)phenyl]-N'-(2-cyclohexyldioxolan-2-yl)methylurea;
N-(2,4-dimethoxyphenyl)-N'-(2-cyclohexyldioxolan-2-yl)methylurea;
N-[2,6-bis(1-methylethyl)phenyl]-N'-(2-cyclohexyl-1,3-dioxan-2-yl)methylurea;
N-[2,6-bis(1-methylethyl)phenyl]-N'-[2-(4,4-dimethylcyclohexyl)-5,5-dimethyl-1,3-dioxan-2-yl]methylurea;
N-[2,6-bis(1-methylethyl)phenyl]-N'-(2-cyclohexylmethyl-5,5-dimethyl-1,3-dioxan-2-yl)methylurea;
N-[2,6-bis(1-methylethyl)phenyl]-N'-(2-cyclopentylmethyl-5,5-dimethyl-1,3-dioxan-2-yl)methylurea;
N-[2,6-bis(1-methylethyl)phenyl]-N'-[(4S,5S)-2-cyclohexyl-4,5-dimethyldioxolan-2-yl]methylurea,
m.p. 161°-162° C. $[\alpha]_D^{26} = +9.1$ (c=0.730, AcOH);
N-[2,6-bis(1-methylethyl)phenyl]-N'-[(2S,4R,5S)-2-cyclohexyl-4,5-dimethyldioxolan-2-yl]methylurea,
m.p. 163°-166° C.;
N-[2,6-bis(1-methylethyl)phenyl]-N'-[(2R,4R,5S)-2-cyclohexyl-4,5-dimethyldioxolan-2-yl]methylurea,
m.p. 174°-177° C.; and
N-(2,6-dimethylphenyl)-N'-[(4R,5R)-2-cyclohexyl-4,5-dimethyldioxolan-2-yl]methylurea, m.p. 198°–200° C.

EXAMPLE 5

To a stirred solution of (2-cyclohexyl-1,3-dithiolan-2-yl)methylamine (2.17 g 0.100 mole) in 40 ml of n-hexane/ethylacetate (5:1) is added dropwise at room temperature 2,6-bis(1-methylethyl)phenylisocyanate (1.94 g 0.105 mole). The reaction mixture is stirred at room temperature for two hours. Precipitated solid is filtered, washed with n-pentane/ether (1:1) and dried, yielding 3.90 g of N-[2,6-bis(1-methylethyl)phenyl]-N'-(2-cyclohexyl-1,3-dithiolan-2-yl)methylurea.

White powder m.p. 184°–186° C.

| Elemental analysis | C | H | N | S |
|---|---|---|---|---|
| Calculated for $C_{23}H_{36}N_2OS_2$ | 65.66 | 8.62 | 6.65 | 15.24 |
| Found | 65.74 | 8.60 | 6.65 | 15.20 |

EXAMPLE 6

To a stirred solution of [2-(4-dimethylaminophenyl)-5,5-dimethyl-1,3-dioxan-2-yl]methylamine (2.64 g 0.100 mole) in 40 ml of ethylacetate is added dropwise at room temperature 2,6-bis(1-methylethyl)phenylisocyanate (1.94 g 0.105 mole). The reaction mixture is stirred at room temperature for two hours. Volatiles are removed under reduced pressure and the residue is crystallized from ethylacetate/n-hexane yielding 4.0 g of N-[2,6-bis(1-methylethyl)phenyl]-N'-[2-(4-dimethylaminophenyl)-5,5-dimethyl-1,3-dioxan-2-yl]methylurea.

White powder m.p. 198°–200° C.

| Elemental analysis | C | H | N |
|---|---|---|---|
| Calculated for $C_{28}H_{41}N_3O_3$ | 71.91 | 8.83 | 8.38 |
| Found | 71.97 | 8.85 | 8.90 |

Analogously the following compounds can be prepared:

N-[2,6-bis(1-methylethyl)phenyl]-N'-(2-phenyl-1,3-dithiolan-2-yl)methylurea;
m.p. 159°–161° C.

N-[2,6-bis(1-methylethyl)phenyl]-N'-(2-phenyl-1,3-dithian-2-yl)methylurea;
m.p. 138°–140° C.

N-[2,6-bis(1-methylethyl)phenyl]-N'-(2-heptyl-1,3-dithiolan-2-yl)methylurea;
m.p. 100°–102° C.

N-[2,6-bis(1-methylethyl)phenyl]-N'-(2-heptyl-5,5-dimethyl-1,3-dioxan-2-yl)methylurea;
m.p. 110°–111° C.

N-[2,6-bis(1-methylethyl)phenyl]-N'-[5,5-dimethyl-2-[4-(imidazol-1-yl)phenyl]-1,3-dioxan-2-yl]methylurea;
m.p. 128°–130° C.

N-[2,6-bis(1-methylethyl)phenyl]-N'-[5,5-dimethyl-2-[3-(imidazol-1-yl)phenyl]-1,3-dioxan-2-yl]methylurea;
m.p. 114°–116° C.

N-[2,6-bis(1-methylethyl)phenyl]-N'-[(4R,5R)-4,5-dimethyl-2-(4-dimethylaminophenyl)-1,3-dioxolan-2-yl]methylurea;
m.p. 165°–167° C. $[\alpha]_D^{22} = -14.1$ (c=0.850, EtOH);

N-[2,6-bis(1-methylethyl)phenyl]-N'-[4,5-dimethyl-2-[4-(1-methylimidazol-2-yl)phenyl]-1,3-dioxolan-2-yl]methylurea;

N-[2,6-diethyl-4-fluorophenyl]-N'-(2-cyclohexyl-1,3-dithiolan-2-yl)methylurea;

N-[2,6-dibromophenyl]-N'-(2-phenyl-1,3-dithian-2-yl)methylurea;

N-[2,6-bis(1-methylethyl)phenyl]-N'-[(2-methylpent-2-en-5-yl)-1,3-dithiolan-2-yl]methylurea;

N-[2,6-bis(1-methylethyl)phenyl]-N'-[(oct-3-en-1-yl)-1,3-dithiolan-2-yl]methylurea;

N-[2,6-bis(1-methylethyl)phenyl]-N'-[2-cyclohexyl)-1,3-dithian-2-yl]methylurea;
m.p. 175°–177° C.

N-[2,6-bis(1-methylethyl)phenyl]-N'-[2-(4-dimethylaminophenyl)-1,3-dithian-2-yl]methylurea;
m.p. 168°–170° C.;

N-[2,6-bis(1-methylethyl)phenyl]-N'-(4,5-dimethyl-2-cyclohexyldithiolan-2-yl)methylurea,
m.p. 175°–178° C.; and N-[2,6-bis(1-methylethyl)phenyl]-N'-[2-(4-dimethylaminophenyl)dithiolan-2-yl]methylurea,
m.p. 154°–156° C.

EXAMPLE 7

With the usual methods of pharmaceutical technique, preparation can be made of capsules having the following composition:

| | |
|---|---|
| N-[2,6-bis(1-methylethyl)phenyl]-N'-(2-cyclohexyl-1,3-dithiolan-2-yl)methylurea | 200 mg |
| Starch | 8 mg |
| Microcrystalline cellulose | 23 mg |
| Talc | 8 mg |
| Magnesium stearate | 5 mg |

We claim:
1. A compound of formula (I)

$$A-(CH_2)_m-\underset{\underset{Y-R_2}{|}}{\overset{\overset{X-R_1}{|}}{C}}-(CH_2)_n-NH-\underset{\underset{Q}{\|}}{C}-NH-B \quad (I)$$

wherein
m is zero, 1 or 2;
n is 1, 2 or 3;
Q is oxygen or sulphur;
X and Y, being the same, are oxygen or sulphur;
A is
  a) a $C_1$–$C_{10}$ saturated or unsaturated, branched or unbranched hydrocarbon chain, unsubstituted or substituted by 1 to 4 substituents independently chosen from halogen, $C_1$–$C_6$ alkyl, trihalo-$C_1$–$C_3$ alkyl and $C_1$–$C_6$ alkoxy;
  b) a $C_3$–$C_7$ cycloalkyl ring unsubstituted or substituted by 1 to 4 substituents independently chosen from halogen, $C_1$–$C_6$ alkyl, trihalo-$C_1$–$C_3$ alkyl and $C_1$–$C_6$ alkoxy;
  c) an aryl group unsubstituted or substituted by one to four subsstituents independently chosen from halogen, $C_1$–$C_6$ alkyl, trihalo-$C_1$–$C_3$ alkyl, hydroxy, $C_1$–$C_6$ alkoxy, $C_1$–$C_6$-alkythio, $C_1$–$C_6$ alkylsulfonyl and $C_1$–$C_4$ di-alkylamino;
  d) an aryl group substituted by two adjacent substituents forming a methylenedioxy group and optionally by 1 to 3 substituents as defined above under c); or
  e) an aryl group substituted by an imidazolyl group, in its turn optionally substituted by $C_1$–$C_4$ alkyl;

each of $R_1$ and $R_2$, independently, is $C_1$-$C_6$ alkyl; or $R_1$ and $R_2$, taken together, are a $C_2$-$C_4$ alkylene chain in which each carbon atom can be optionally substituted by 1 or 2 substituents independently chosen from halogen and $C_1$-$C_4$ alkyl;

B is an aryl group unsubstituted or substituted by 1 to 4 substituents independently chosen from halogen, $C_1$-$C_6$ alkyl, trihalo-$C_1$-$C_3$ alkyl, $C_1$-$C_6$ alkoxy, $C_1$-$C_6$ alkylthio, and $C_1$-$C_6$ alkylsulfonyl; and the pharmaceutically acceptable salts thereof.

2. A compound of formula (I), according to claim 1, wherein m is zero or 1;
n is 1, 2 or 3;
Q is oxygen or sulphur;
X and Y, being the same, are oxygen or sulphur;
$R_1$ and $R_2$, taken together, form a $C_2$-$C_4$ alkylene chain in which each carbon atom can be unsubstituted or substituted by one or two substituents independently chosen from halogen and $C_1$-$C_4$ alkyl;
A is
  a') a branched or unbranched $C_4$-$C_7$ hydrocarbon chain optionally containing 1 or 2 double bonds, unsubstituted or substituted by one or two substituents chosen independently from halogen and trifluoromethyl;
  b') a cyclopentyl or cyclohexyl ring unsubstituted or substituted by one or two substituents chosen independently from halogen and $C_1$-$C_4$ alkyl;
  c') a phenyl or pyridyl ring unsubstituted or substituted by one or two substituents independently chosen from halogen, $C_1$-$C_4$ alkyl, trifluoromethyl, hydroxy, $C_1$-$C_4$ alkoxy, $C_1$-$C_4$ alkylsulfonyl and $C_1$-$C_4$ di-alkylamino;
  d') a phenyl ring substituted by two adjacent substituents forming a methylenedioxy group and optionally by one or two substituents as defined above under c'); or
  e') a phenyl ring substituted by an imidazolyl group, in its turn optionally substituted by $C_1$-$C_4$ alkyl;
B is a phenyl ring unsubstituted or substituted by one or two substituents independently chosen from halogen, $C_1$-$C_4$ alkyl and $C_1$-$C_4$ alkoxy; and the pharmaceutically acceptable salts thereof.

3. A compound of formula (I), according to claim 1, wherein
m is zero or 1;
n is 1 or 2;
Q is oxygen;
X and Y, being the same, are oxygen;
$R_1$ and $R_2$, taken together, from a $C_2$-$C_3$ alkylene chain in which at least one carbon atom is substituted by one or two substituents independently chosen from halogen and $C_1$-$C_4$ alkyl;
A is a $C_4$-$C_7$ alkyl chain; a cyclopentyl or cyclohexyl ring unsubstituted or substituted by one or two substituents independently chosen from halogen and $C_1$-$C_4$ alkyl; or a phenyl or pyridyl ring unsubstituted or substituted by one or two substituents independently chosen from halogen, $C_1$-$C_4$ alkyl, hydroxy and $C_1$-$C_4$ alkyl di-alkylamino;
B is a phenyl ring substituted by one or two substituents independently chosen from halogen and $C_1$-$C_4$ alkyl; and the pharmaceutically acceptable salts thereof.

4. A compound of formula (I), according to claim 1, wherein
m is zero or 1;
n is 1 or 2;
Q is oxygen;
X and Y, being the same, are sulphur;
$R_1$ and $R_2$, taken together, form a $C_2$-$C_3$ alkylene chain in which each carbon atom can be unsubstituted or substituted independently by one or two substituents independently chosen from halogen and $C_1$-$C_4$ alkyl;
A is a $C_4$-$C_7$ alkyl chain; a cyclopentyl or cyclohexyl ring unsubstituted or substituted by one or two substituents independently chosen from halogen and $C_1$-$C_4$ alkyl;
B is a phenyl ring substituted by one or two substituents independently chosen from halogen and $C_1$-$C_4$ alkyl; and the pharmaceutically acceptable salts thereof.

5. A compound selected from
N-[2,6-bis(1-methylethyl)phenyl]-N'-(2-phenyldioxolan-2-yl)methylurea;
N-[2,6-bis(1-methylethyl)phenyl]-N'-(5,5-dimethyl-2-phenyl-1,3-dioxan-2-yl)methylurea;
N-[2,6-bis(1-methylethyl)phenyl]-N'-[5,5-dimethyl-2-(4-fluorophenyl)-1,3-dioxan-2-yl]methylurea;
N-[2,6-bis(1-methylethyl)phenyl]-N'-[4,5-dimethyl-2-phenyldioxolan-2-yl]methylurea;
N-[2,6-bis(1-methylethyl)phenyl]-N'-[5,5-diethyl-2-phenyl-1,3-dioxan-2-yl]methylurea;
N-[2,6-bis(1-methylethyl)phenyl]-N'-[2-cyclohexyl-5,5-dimethyl-1,3-dioxan-2-yl]methylurea;
N-[2,6-bis(1-methylethyl)phenyl]-N'-[2-cyclohexyl-4,5-dimethyl-dioxolan-2-yl]methylurea;
N-[2,6-bis(1-methylethyl)phenyl]-N'-[2-cyclopentyl-5,5-dimethyl-1,3-dioxan-2-yl]methylurea;
N-[2,6-bis(1-methylethyl)phenyl]-N'-(2-cyclohexyl-5,5-diethyl-1,3-dioxan-2-yl)methylurea;
N-[2,6-bis(1-methylethyl)phenyl]-N'-(2-cyclohexyl-1,3-dithiolan-2-yl)methylurea;
N-[2,6-bis(1-methylethyl)phenyl]-N'-[2-(4-dimethylaminophenyl)-5,5-dimethyl-1,3-dioxan-2-yl]methylurea;
N-[2,6-bis(1methylethyl)phenyl]-N'-[2-cyclohexyl-1,3-dithian-2-yl]methylurea;
N-[2,6-bis(1-methylethyl)phenyl]-N'-[2-phenyl-1,3-dithiolan-2-yl]methylurea;
N-[2,6-bis(1-methylethyl)phenyl]-N'-(2-phenyl-1,3-dithian-2-yl)methylurea;
N-[2,6-bis(1-methylethyl)phenyl]-N'-(2-heptyl-1,3-dithiolan-2yl)methylurea;
N-[2,6-bis(1-methylethyl)phenyl]-N'-(2-heptyl-5,5-dimethyl-1,3-dioxan-2-yl)methylurea;
N-[2,6-bis(1-methylethyl)phenyl]-N'-[4,5-dimethyl-2-(4-dimethylaminophenyl)-1,3-dioxolan-2-yl]methylurea;
N-[2,6-bis(1-methylethyl)phenyl]-N'-[2-(4-dimethylaminophenyl)-1,3-dithian-2-yl]methylurea;
N-[2,6-bis(1-methylethyl)phenyl]-N'-(4,5-dimethyl-2-cyclohexyldithiolan-2-yl)methylurea; and
N-[2,6-bis(1-methylethyl)phenyl]-N'-[2-(4-dimethylaminophenyl)dithiolan-2-yl]methylurea;
if the case either as a single isomer or as a mixture of isomers thereof, and the pharmaceutically acceptable salts thereof.

6. A pharmaceutical composition comprising a suitable carrier and/or diluent and, as an active principle, a compound of formula (I) as claimed in claim 1, or a pharmaceutically acceptable salt thereof.

7. A method for preventing coronary heart disease, comprising administering to a patient a coronary heart disease preventing amount of a compound of formula (I), as defined in claim 1, or a pharmaceutically acceptable salt thereof.

8. A method of administering an antidyslipidaemic treatment, comprising administering to a patient an antidyslipidaemic effective amount of a compound of formula (I), as defined in claim 1, or a pharmaceutically acceptable salt thereof.

9. A method of administering an antiatheroschlerotic treatment, comprising administering to a patient an antiatheroschlerotic effective amount of a compound of formula (I), as defined in claim 1, or a pharmaceutically acceptable salt thereof.

* * * * *

UNITED STATES PATENT AND TRADEMARK OFFICE
CERTIFICATE OF CORRECTION

PATENT NO. : 5,264,441

DATED : November 23, 1993

INVENTOR(S) : Paolo COZZI et al

It is certified that error appears in the above-identified patent and that said Letters Patent is hereby corrected as shown below:

On the title page: Inventor,
Under Item [75], change "Danielle" to -- DANIELE --

Signed and Sealed this

Twentieth Day of September, 1994

Attest:

BRUCE LEHMAN

Attesting Officer

Commissioner of Patents and Trademarks